(12) United States Patent
Govari et al.

(10) Patent No.: US 12,733,999 B2
(45) Date of Patent: Sep. 15, 2026

(54) TRAINING SYSTEM FOR A NEURAL NETWORK TO GUIDE A ROBOTIC ARM TO OPERATE A CATHETER

(71) Applicant: BIOSENSE WEBSTER (ISRAEL) LTD., Yokneam (IL)

(72) Inventors: Assaf Govari, Haifa (IL); Andres Claudio Altmann, Haifa (IL); Vadim Gliner, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 535 days.

(21) Appl. No.: 17/965,061

(22) Filed: Oct. 13, 2022

(65) Prior Publication Data

US 2023/0128764 A1 Apr. 27, 2023

Related U.S. Application Data

(60) Provisional application No. 63/271,270, filed on Oct. 25, 2021.

(51) Int. Cl.
*A61B 34/32* (2016.01)
*A61B 34/00* (2016.01)
(Continued)

(52) U.S. Cl.
CPC .............. *A61B 34/32* (2016.02); *A61B 34/74* (2016.02); *B25J 9/161* (2013.01); *B25J 9/163* (2013.01);
(Continued)

(58) Field of Classification Search
CPC . A61B 34/32; A61B 34/74; A61B 2034/2051; A61B 2034/2059; A61B 2034/301; G16H 40/63; B25J 9/161; B25J 9/163; G05B 2219/33027; G05B 2219/39001
See application file for complete search history.

(56) References Cited

U.S. PATENT DOCUMENTS 5,391,199 A 2/1995 Ben-Haim
6,239,724 B1 5/2001 Doron et al.
(Continued)

FOREIGN PATENT DOCUMENTS

AU 2005200375 A1 * 9/2005
CN 103874525 A 6/2014
(Continued)

OTHER PUBLICATIONS

Locke et al., "Optimal Remote Center-of-Motion Location for Robotics Assisted Minimally-Invasive Surgery". 2007 IEEE Int Con on Robotics and Automation. Rome Italy, Apr. 10-14, 2007. https://citeseerx.ist.psu.edu/document?repid=rep1&type=pdf&doi=38cca2f7a9267da4e829ab51cddbd8970673651 (Year: 2007).*
(Continued)

*Primary Examiner* — Shaun L David
*Assistant Examiner* — Cherie M Poland
(74) *Attorney, Agent, or Firm* — Clayton, McKay & Bailey, PC

(57) ABSTRACT

Methods and systems are provided for training machine learning (e.g., NN) or other artificial intelligence (AI) models to control a robot arm to manipulate a catheter to robotically perform an invasive clinical catheter-based procedure.

16 Claims, 2 Drawing Sheets

(51) Int. Cl.
*A61B 34/20* (2016.01)
*A61B 34/30* (2016.01)
*B25J 9/16* (2006.01)
*G16H 40/63* (2018.01)

(52) U.S. Cl.
CPC ...... *G16H 40/63* (2018.01); *A61B 2034/2051* (2016.02); *A61B 2034/2059* (2016.02); *A61B 2034/301* (2016.02); *G05B 2219/33027* (2013.01); *G05B 2219/39001* (2013.01)

(56) References Cited

U.S. PATENT DOCUMENTS

| | | | | |
|---|---|---|---|---|
| 6,332,089 | B1 | 12/2001 | Acker et al. | |
| 6,484,118 | B1 | 11/2002 | Govari | |
| 6,618,612 | B1 | 9/2003 | Acker et al. | |
| 6,690,963 | B2 | 2/2004 | Ben-Haim et al. | |
| 8,046,049 | B2 | 10/2011 | Govari et al. | |
| 8,456,182 | B2 | 6/2013 | Bar-Tal et al. | |
| 10,931,643 | B1 | 2/2021 | Neumann | |
| 11,096,753 | B1 * | 8/2021 | Mantri | A61B 90/03 |
| 2002/0065455 | A1 | 5/2002 | Ben-Haim et al. | |
| 2003/0120150 | A1 | 6/2003 | Govari | |
| 2004/0024311 | A1 * | 2/2004 | Quaid, III | A61B 90/39 600/428 |
| 2004/0068178 | A1 | 4/2004 | Govari | |
| 2010/0160770 | A1 | 6/2010 | Govari et al. | |
| 2010/0256558 | A1 * | 10/2010 | Olson | A61B 34/77 604/95.01 |
| 2014/0046128 | A1 * | 2/2014 | Lee | A61B 34/30 600/102 |
| 2018/0014891 | A1 * | 1/2018 | Krebs | A61B 34/20 |
| 2018/0296281 | A1 | 10/2018 | Yeung | |
| 2018/0353253 | A1 * | 12/2018 | Bowling | A61B 34/30 |
| 2019/0206563 | A1 * | 7/2019 | Shelton, IV | G16H 50/20 |
| 2020/0297444 | A1 | 9/2020 | Camarillo | |
| 2021/0121251 | A1 | 4/2021 | Aljuri | |
| 2021/0186602 | A1 | 6/2021 | Govari | |
| 2022/0148454 | A1 | 5/2022 | Jaramaz | |
| 2022/0192758 | A1 | 6/2022 | Roh | |

FOREIGN PATENT DOCUMENTS

| | | | |
|---|---|---|---|
| CN | 109077752 | A | 12/2018 |
| CN | 111931626 | A | 11/2020 |
| EP | 3409230 | A1 | 12/2018 |
| KR | 20200006251 | A | 1/2020 |
| WO | 9605768 | A1 | 2/1996 |
| WO | 2020030722 | A1 | 2/2020 |

OTHER PUBLICATIONS

European Search report for corresponding EPA No. 22203167.6 dated Feb. 24, 2023.

Translation of CN Office Action and Search Report from CN Application No. 202211309498.0 dated Aug. 21, 2025.

Notice of Allowance received in CN Application No. 202211309498.0 dated Apr. 29, 2026.

* cited by examiner

TRAINING SYSTEM FOR A NEURAL NETWORK TO GUIDE A ROBOTIC ARM TO OPERATE A CATHETER

CROSS-REFERENCE TO RELATED APPLICATIONS

This application claims the benefit of U.S. Provisional Patent Application 63/271,270, filed October, 2021, whose disclosure is incorporated herein by reference.

FIELD OF THE INVENTION

This invention relates generally to robotic surgery, and specifically to automatic guiding and maneuvering of a catheter coupled to a robotic arm by a neural network (NN).

BACKGROUND OF THE INVENTION

Controlling medical robotic systems was previously suggested in the patent literature. For example, U.S. Patent Application Publication 2014/0046128 describes a control method that may be applied to a surgical robot system including a slave robot having a robot arm to which a main surgical tool and an auxiliary surgical tool are coupled, and a master robot having a master manipulator to manipulate the robot arm. The control method includes acquiring data regarding a motion of the master manipulator, predicting a basic motion to be performed by an operator based on the acquired motion data and results of learning a plurality of motions constituting a surgical task, and adjusting the auxiliary surgical tool so as to correspond to the operator basic motion based on the predicted basic motion. The control method allows an operator to perform surgery more comfortably and to move or fix all required surgical tools to or at an optimized surgical position.

As another example, U.S. Patent Application Publication 2021/0121251 describes an apparatus for robotic surgery that comprises a processor configured with instructions to receive patient data from treated patients, receive surgical robotics data for each of the plurality of treated patients, and output a treatment plan of a patient to be treated in response to the patient data and the surgical robotics data. This approach has the advantage of accommodating individual variability among patients and surgical system parameters so as to provide improved treatment outcomes.

U.S. Patent Application Publication 2020/0297444 describes certain aspects related to systems and techniques for localizing and/or navigating a medical instrument within a luminal network. A medical system can include an elongate body configured to be inserted into the luminal network, as well as an imaging device positioned on a distal portion of the elongate body. The system may include memory and processors configured to receive from the imaging device image data that includes an image captured when the elongate body is within the luminal network. The image can depict one or more branchings of the luminal network. The processor can be configured to access a machine learning model of one or more luminal networks and determine, based on the machine learning model and information regarding the one or more branchings, a location of the distal portion of the elongate body within the luminal network.

The present disclosure will be more fully understood from the following detailed description of the embodiments thereof, taken together with the drawings, in which:

DETAILED DESCRIPTION OF EMBODIMENTS

Overview

Figure 1:
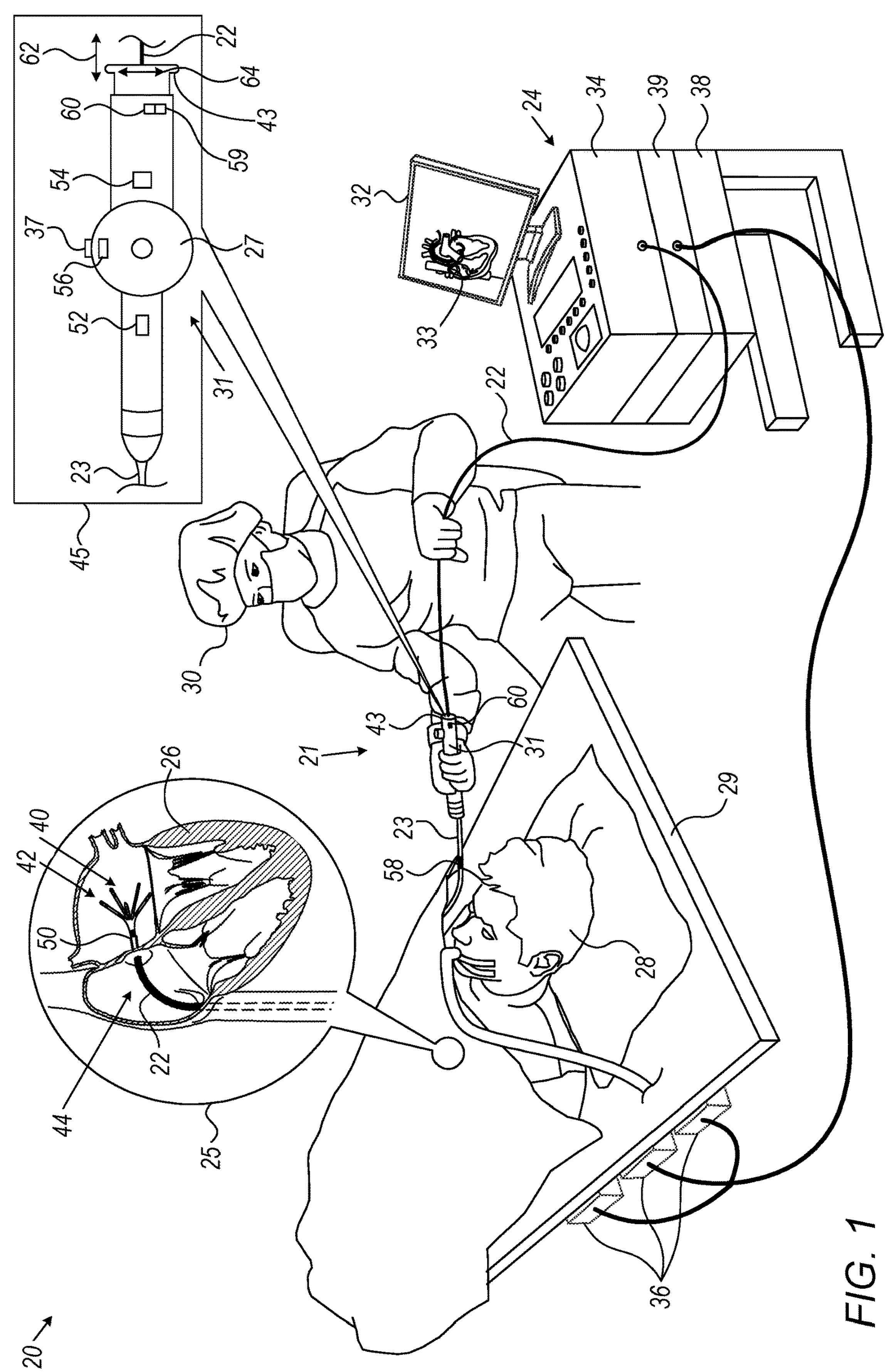
FIG. 1 is a schematic, pictorial illustration of a training system for a neural network (NN) to guide a robotic arm to operate a cardiac catheter, in accordance with an embodiment of the present invention.

A probe, e.g., a catheter, such as a cardiac catheter, is typically manipulated manually by a physician operating a handpiece (e.g., a handle equipped with controls such as knobs and actuators) in order to position the probe correctly inside an organ such as a heart. For example, to diagnose and treat an arrhythmia, a physician may need to insert a multi-electrode catheter into the heart of the patient, to measure intracardiac signals via the catheter, and apply ablation according to findings. To this end, the physician has to be highly skillful in operating the catheter, while at the same time working under heavy workload conditions that limit physician availability.

To increase availability of catheterization procedures in general, and cardiac catheter-based procedures in particular, some embodiments of the disclosed technique envision catheter manipulation performed by a robotic arm operated by a neural network (NN) that translates high level requests from a physician for a particular catheter operation (e.g., by specifying a target anatomical structure to be approached) into actions by the robotic arm operating the handpiece. Such hands-free robotic control requires a set of training data for the NN in order to train the robotic system, training data which is currently absent.

Embodiments of the present invention that are described hereafter provide methods and systems for training machine learning (e.g., NN) or other artificial intelligence (AI) models to control a robot arm to manipulate a catheter to robotically perform an invasive clinical catheter-based procedure.

Some embodiments of the invention provide one or more training setups, each training setup comprising a set of sensors attached to the handpiece of a probe (e.g., catheter) used by the physician performing an invasive procedure. The sensors record the motions of the handpiece, i.e., as its operation causes a distal end of the catheter to be translated, directed, rotated and locked in place. The sensors also track activation and operation of elements of the handpiece by the physician, e.g., a knob used to deflect the distal end of the catheter. The term "handpiece" generally refers hereinafter to a proximal section of a probe handle disposed with controls, but the "handpiece" may also include a proximal section of a shaft and/or a sheath of the probe in the vicinity of the handle, which the physician may manipulate as well. As the handpiece is manipulated by the physician, the readouts of the sensors are recorded, as are the corresponding locations of the catheter from the catheter sensors.

The one or more training setups of the disclosed training system are used by one or more (typically many) physicians, and the training data acquired from each physician's actions is recorded and assembled into a set of data used to train (e.g., teach) an NN.

The sensors may be numerous and of different types, such as magnetic sensors, electrical sensors, "encoding" sensors—i.e., those that use an encoder, and more. A detailed embodiment of such a training system with its particular sensors is described in FIG. 1.

Training targets are clinical actions, such as arriving at a target location, and an NN optimization process (e.g., defined by a loss function) can be achieved by reaching a target using a minimal number of catheter actions performed the via handpiece or using a minimal amount of spatial movement of the distal end in each operational step. As an example, a catheter task is assumed to be anatomically mapping an atrium volume of 8×8×8 cm with a resolution of 2 mm, i.e., including 64,000 voxels. The operating physician wants the cardiac catheter to move, and provides two voxel numbers to the net: a start position (e.g., voxel 15) and an end position (e.g., voxel 2050). In this embodiment, the NN has to be trained to find the closest movement, or series of movements, from a given start location to a given end location (for example, it may find a double movement from a location (e.g., position, direction and roll angle) voxel 15 to voxel 350, and then from 350 to 2050, or a single movement from voxel 15 to 2050). Once the NN chooses the closest (i.e., minimal) movement(s), it outputs commands to the robot corresponding to motions of the handpiece, i.e., translation (e.g., advancement/retraction), deflection, and rotation of the distal end of the catheter's shaft using controls over the handpiece.

To have the above motions commanded by the NN accurately and consistently enough to fit varying patient anatomies, at least several tens of NN training data sets are envisaged to be collected. However, as hundreds of such procedures may be performed over a year, the training systems can readily accomplish a very extensive and robust training data cohort.

System Description

FIG. 1 is a schematic, pictorial illustration of a training system 20 for a neural network (NN) to guide a robotic arm to operate a cardiac catheter, in accordance with an embodiment of the present invention. FIG. 1 depicts a physician 30 using a multi-arm Pentaray® catheter 21 to perform mapping and/or ablation of a heart 26 of a patient 28 on a surgical table 29. As inset 25 shows, catheter 21 comprises, at its distal end, a multi-arm distal end assembly 40 coupled with electrodes 42. During the catheterization procedure, electrodes 42 acquire and/or inject electrical signals from and/or to the tissue of heart 26. Distal end assembly 40 is further coupled with a magnetic location sensor 50, which is configured to output signals indicative of distal end assembly 40's position, direction and roll angle inside heart 26.

Using sensor 50, a processor 34 in a console 24 can therefore determine the position, direction and roll angle of the distal end assembly. For this purpose, console 24 further comprises a driver circuit 39, which drives magnetic field generators 36 placed at known positions external to patient 28, e.g., below the patient's torso. Physician 30 can view the location of distal end assembly 40 in an image 33 of heart 26 on a user display 32.

The method of magnetic location sensing is implemented, for example, in the CARTO™ system, produced by Biosense Webster, and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Further to magnetic location tracking, during the procedure an electrical location tracking system may be used to track the respective locations of electrodes 42, by associating each electrode-acquired location signal with a cardiac location at which the signal was acquired. For example, the Active Current Location (ACL) system, made by Biosense-Webster (Irvine, California), which is described in U.S. Pat. No. 8,456,182, whose disclosure is incorporated herein by reference, may be used. In the ACL system, a processor estimates the respective locations of electrodes 42 based on impedances measured between each of the catheter electrodes 42, and a plurality of surface electrodes (not shown) that are coupled to the skin of patient 28.

Physician 30 navigates distal end assembly 40 that is mounted on a shaft 22 to a target location in heart 26 by holding catheter handle 31 with a right hand, and manipulating shaft 22 by advancing the shaft with a left hand or using a thumb control 43 near the proximal end of handle 31 and/or deflection from the sheath 23.

As inset 45 shows, handle 31 further comprises a knob 27 having a lock button 37, which physician 30 also uses for manipulating shaft 22. A set of sensors 52-60, described below, is coupled to catheter 21 in various locations to track the physician's operations. In particular, multiple sensors 52-60 record the motions of handle 31, of a proximal section of sheath 23, and shaft 22, i.e., as physician 30 translates and rotates catheter 21 during the catheterization procedure. The above-described operation of catheter 21 by physician 30 is collectively named hereinafter "manipulating the handpiece," and the purpose of system 20 is to generate location data that enables a training of an NN to be used by a processor to guide a catheter using a robotic arm, as described in FIG. 2.

By way of example, elements of the handpiece e.g., knob 27 used to deflect (44) (i.e., redirect by variably curving) a distal end of shaft 22 of the catheter and button 37 to lock it in place, and thumb control 43 to advance or retract (62) shaft 22 as well rotate (64) shaft 22, are activated by the physician. As the handpiece is manipulated by the physician, the readouts of sensors 52-60 are recorded, as are the corresponding locations of the catheter (from sensor 50 on the catheter and/or from the advanced location current (ACL) readouts).

In the shown embodiment, sensor 52 is a magnetic sensor configured to indicate position, direction and roll angle of handle 31. Sensor 54 is an encoding sensor configured to indicate the amount and direction of knob 27 rotation. Sensor 56 is configured to indicate the timings and durations of using push button 37. Sensor 58 is a magnetic sensor configured to indicate position, direction and roll angle of a proximal section of sheath 23. Sensor 60 is an encoding sensor configured to indicate the amount and direction of shaft 22 distal or proximal motion 62. Sensor 59 is an encoding senor configured to indicate the amount and direction of shaft 22 rotation 64 about its longitudinal axis. The entire recorded catheter location information is stored in a memory 38 in console 24, to be used during training of an NN, as described in FIG. 2.

The example illustration shown in FIG. 1 is chosen purely for the sake of conceptual clarity. Additional or alternative sensor locations of sensors 52-60 may be used. Other types of sensors and catheters may equivalently be employed during training. The sensors can sense one or more actions of actuators located at the handpiece.

Contact with tissue sensors may be fitted at distal end assembly 40. In an embodiment, processor 34 is further configured to indicate the quality of physical contact between each of the electrodes 42 and an inner surface of the cardiac tissue during measurement.

Processor 34 typically comprises a general-purpose computer with software programmed to carry out the functions described herein. In particular, processor 34 runs a dedicated algorithm as disclosed herein, including in FIG. 2, that enables processor 34 to perform the disclosed steps, as further described below. The software may be downloaded to the computer in electronic form, over a network, for example, or it may, alternatively or additionally, be provided and/or stored on non-transitory tangible media, such as magnetic, optical, or electronic memory.

Training an NN to Guide a Robotic Arm to Operate a Catheter

Figure 2:
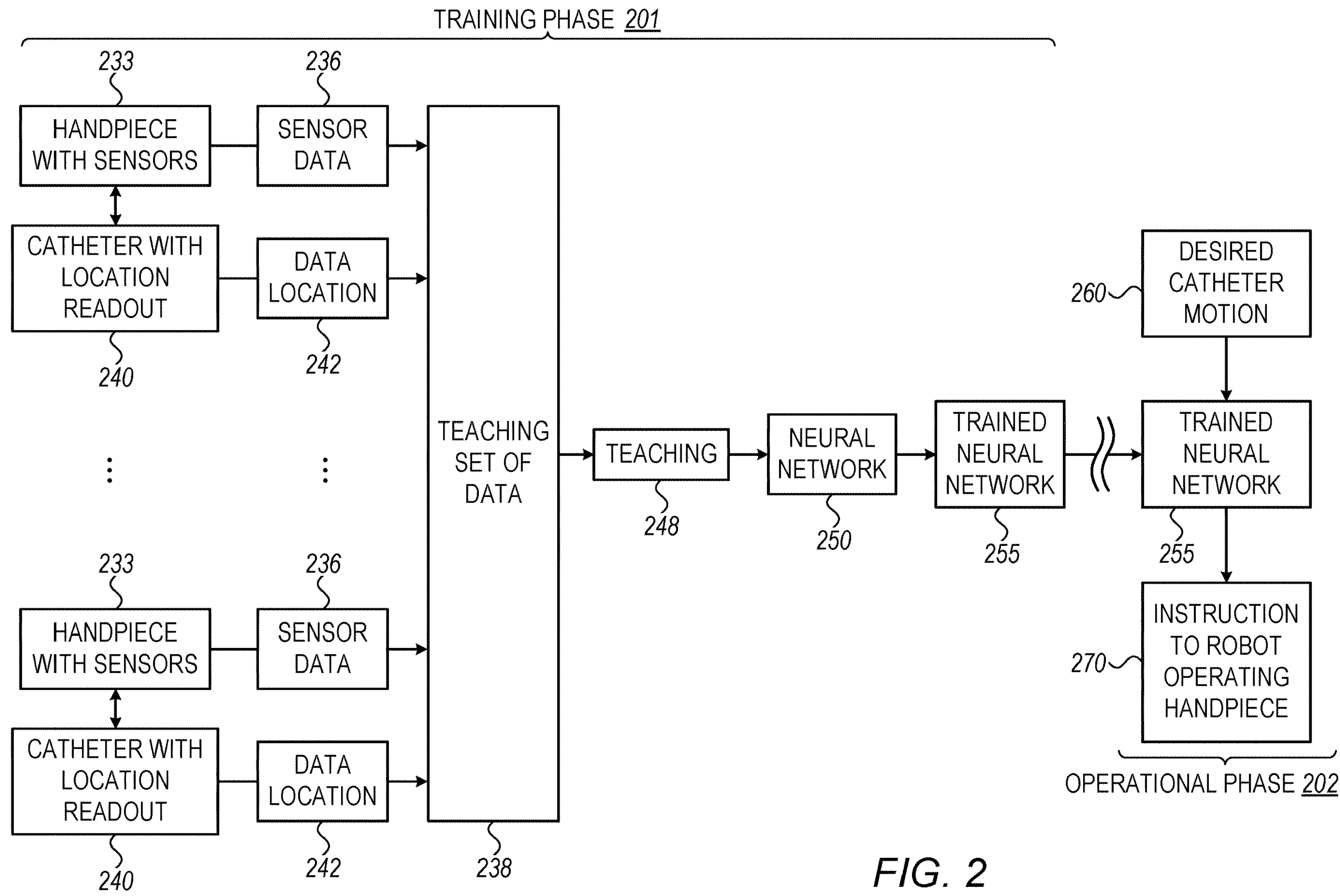
FIG. 2 is a combined block diagram and flow chart that together schematically illustrate a method and algorithm for training and using an NN to guide a robotic arm to operate a catheter, according to an embodiment of the present invention.

FIG. 2 is a combined block diagram and flow chart that together schematically illustrate a method and algorithm for training and using an NN 250 to guide a robotic arm to operate a catheter, according to an embodiment of the present invention. The combined block diagram and flow chart is divided into two phases: a training phase 201 and an operational phase 202.

Training phase 201 involves collection of training data from multiple training systems, such as system 20 of FIG. 1 and/or from multiple procedures performed on a system such as training system 20. The recorded training data comprises two corresponding data sets:

A first data set 236: the probe handpiece sensors 233 (e.g., handpiece of catheter 21 of FIG. 1 with sensors 52-60) and, a second data set 242: from catheter location readout 240 of the distal and of the probe inside an organ (e.g., respective position, direction and roll-angle of distal end assembly 40 of catheter 21 inside hearth 26)

Multiple data sets 236 and 242 are stored in a memory, such as memory 38 of system 20, to be used for training NN 250 to become a trained NN 255.

Operational phase 202 involves using a trained NN in a system that comprises a probe coupled to a robotic arm. Such system is described, for example, in U.S. Pat. No. 8,046,049 that describes an apparatus for use with a steerable catheter that includes a thumb control which can be adapted to control, for example, movement of a shaft or a deflection of a distal tip of the catheter. The apparatus includes a robot with an end-effector adapted to be coupled to the thumb control, such as thumb control 43 or a knob 27, to advance/retract and/or deflect the distal tip, such as distal assembly 40. U.S. Pat. No. 8,046,049 is assigned to the assignee of the current patent application, and its disclosure is incorporated herein by reference.

As seen in FIG. 2, during operation phase 202, the physician communicates desired catheter motion 260. For example, a physician, such as physician 30, may command mapping of a cardiac chamber and/or ablation therein (e.g., of an ostium of a pulmonary vein). NN 250, which was trained (i.e., taught 248) using a collection 238 of data sets from numerous cardiac chamber mapping and/or ablation sessions, converts the high-level instruction 260 into actual commands 270 to the robotic arm, to manipulate the catheter as learned.

The example combined block diagram and flow chart shown in FIG. 2 is chosen purely for the sake of conceptual clarity. The present embodiment may also comprise additional steps of the algorithm, such as confirmation request steps. These and other possible steps are omitted from the disclosure herein purposely in order to provide a more simplified figure.

Although the embodiments described herein mainly address cardiac catheter-based application, the methods and systems described herein can also be used in training any medical robotic arm to operate a probe coupled to the robotic arm.

EXAMPLES OF EMBODIMENTS

Example 1

An embodiment of the present invention that is described hereinafter provides a training system (20) including one or more training setups and a processor (34). Each of the one or more training setups includes a probe (21) for insertion into an organ, the probe including (i) multiple sensors (52-60) located at a handpiece (31) of the probe, the sensors configured to sense probe operation by a physician performing an invasive procedure using the probe, and (ii) a distal sensor (50) located at a distal end of the probe (21) and configured to indicate a position of the distal end inside the organ corresponding to the probe operation. The processor (34) is configured to (a) receive, from the one or more training setups, probe operation data acquired using the multiple sensors (52-60) and the respective distal sensor (50) of each training setup, and (b) using the probe operation data, train a machine learning (ML) model (250) to guide a robotic arm to operate the probe to perform the invasive procedure.

Example 2

The training system according to example 1, wherein the sensors (52-60) at the handpiece (31) are configured to sense at least one probe operation type selected from a group of types consisting of a position adjustment, a direction adjustment and a roll angle adjustment of the distal end of the probe (21).

Example 3

The training system according to any of examples 1 and 2, wherein the sensors (52-60) at the handpiece (31) are configured to sense at least one probe operation type selected from a group of types consisting of advancing, retracting, deflecting and rotating of the distal end of a shaft of the probe (21).

Example 4

The training system according to any of examples 1 through 3, wherein the sensors (52-60) at the handpiece (310 are configured to sense the probe operation by sensing one or more actions of actuators located at the handpiece.

Example 5

The training system according to example 4, wherein the actuators comprise at least one of a distal section of a sheath of the probe, a thumb control, a knob, and a lock button.

Example 6

The training system according to any of examples 1 through 5, wherein the sensors at the handpiece and the distal sensor are one of magnetic, electric and encoding sensors.

Example 7

The training system according to any of examples 1 through 6, wherein the processor (34) is configured to train the ML model (250) to find a minimal number of movements from a given start location in the organ to a given end location of the distal end of the probe in the organ.

Example 8

The training system according to any of examples 1 through 7, wherein the ML model (250) is a neural network (NN).

Example 9

A training method includes, in each of one or more training setups, inserting a probe (21) into an organ, the probe including multiple sensors (52-60) located at a handpiece (31) of the probe, the sensors configured to sense probe operation by a physician performing an invasive procedure using the probe. The probe (21) further includes a distal sensor (50) located at a distal end of the probe and configured to indicate a position of the distal end inside the organ corresponding to the probe (21) operation. Probe operation data is received from the one or more training setups, the data acquired using the multiple sensors (52-60) and the respective distal sensor (50) of each training setup. using the probe operation data, training a machine learning (ML) model (250) to guide a robotic arm to operate the probe (21) to perform the invasive procedure.

It will be thus appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A training system, comprising:

one or more training setups, each training setup comprising:

a catheter for insertion into a heart, the catheter comprising:

multiple sensors located at a handpiece of the catheter, the sensors configured to sense manual operations of a physician performing a heart procedure using the catheter; and a distal sensor located at a distal end of the catheter and configured to indicate a position of the distal end inside the heart corresponding to the manual operations; and a processor, configured to:

receive, from the one or more training setups, manual operations data acquired using the multiple sensors and the respective distal sensor of each training setup; and using the manual operations data, train a machine learning (ML) model to guide a robotic arm to operate the handpiece of the catheter, in an absence of concurrent manual operations of the physician, to perform the heart procedure.

2. The training system according to claim 1, wherein the sensors at the handpiece are configured to sense at least one manual operation type selected from a group of types consisting of a position adjustment, a direction adjustment and a roll angle adjustment of the distal end of the catheter.

3. The training system according to claim 1, wherein the sensors at the handpiece are configured to sense at least one manual operation type selected from a group of types consisting of advancing, retracting, deflecting and rotating of the distal end of a shaft of the catheter.

4. The training system according to claim 1, wherein the sensors at the handpiece are configured to sense the manual operations by sensing one or more actions of actuators located at the handpiece.

5. The training system according to claim 4, wherein the actuators comprise at least one of a distal section of a sheath of the catheter, a thumb control, a knob, and a lock button.

6. The training system according to claim 1, wherein the sensors at the handpiece and the distal sensor are one of magnetic, electric and encoding sensors.

7. The training system according to claim 1, wherein the processor is configured to train the ML model to find a minimal number of movements from a given start location in the heart to a given end location of the distal end of the catheter in the heart.

8. The training system according to claim 1, wherein the ML model is a neural network (NN).

9. A training method, comprising:

in each of one or more training setups, inserting a catheter into a heart, the catheter comprising:

multiple sensors located at a handpiece of the catheter, the sensors configured to sense manual operations of a physician performing a heart procedure using the catheter; and a distal sensor located at a distal end of the catheter and configured to indicate a position of the distal end inside the heart corresponding to the manual operations;

receiving, from the one or more training setups, manual operations data acquired using the multiple sensors and the respective distal sensor of each training setup; and using the manual operations data, training a machine learning (ML) model to guide a robotic arm to operate the handpiece of the catheter, in an absence of concurrent manual operations of the physician, to perform the heart procedure.

10. The training method according to claim 9, wherein the sensors at the handpiece are configured to sense at least one manual operation type selected from a group of types consisting of a position adjustment, a direction adjustment and a roll angle adjustment of the distal end of the catheter.

11. The training method according to claim 9, wherein the sensors at the handpiece are configured to sense at least one manual operation type selected from a group of types consisting of advancing, retracting, deflecting and rotating of the distal end of a shaft of the catheter.

12. The training method according to claim 9, wherein the sensors at the handpiece are configured to sense the manual operation by sensing one or more actions of actuators located at the handpiece.

13. The training method according to claim 12, wherein the actuators comprise at least one of a distal section of a sheath of the catheter, a thumb control, a knob, and a lock button.

14. The training method according to claim 9, wherein the sensors at the handpiece and the distal sensor are one of magnetic, electric and encoding sensors.

15. The training method according to claim 9, wherein training the ML model comprises training the ML model to find a minimal number of movements from a given start location in the heart to a given end location of the distal end of the catheter in the heart.

16. The training method according to claim 9, wherein the ML model is a neural network (NN).

* * * * *